US005813400A

United States Patent [19]

Bühlmann et al.

[11] Patent Number: 5,813,400

[45] Date of Patent: Sep. 29, 1998

[54] BREATHING APPARATUS

[75] Inventors: Pierre Bühlmann, Lidingö; Ivan Hellquist, Sollentuna, both of Sweden

[73] Assignee: Comasec International S.A., Saint Denis, France

[21] Appl. No.: 674,794

[22] Filed: Jul. 3, 1996

[30] Foreign Application Priority Data

Jul. 5, 1995 [SE] Sweden .................................. 9502441

[51] Int. Cl.[6] .................................................... A61M 16/00

[52] U.S. Cl. ................................ 128/204.23; 128/204.26; 128/205.14

[58] Field of Search ......................... 128/205.13, 205.14, 128/205.16, 204.26, 204.23

[56] References Cited

U.S. PATENT DOCUMENTS

| | | | |
|---|---|---|---|
| 3,827,432 | 8/1974 | Lundgren et al. | 128/205.14 |
| 4,031,887 | 6/1977 | Botos et al. | 128/205.12 |
| 4,108,171 | 8/1978 | Nyman et al. | 128/205.16 |
| 4,141,353 | 2/1979 | Dahlback et al. | 128/202.22 |
| 5,005,570 | 4/1991 | Perkins | 128/204.23 |
| 5,038,770 | 8/1991 | Perkins | 128/204.23 |
| 5,038,772 | 8/1991 | Kolbe et al. | 128/205.16 |
| 5,076,267 | 12/1991 | Pasternack | 128/205.16 |

FOREIGN PATENT DOCUMENTS

| | | |
|---|---|---|
| 7502855 | 10/1976 | Sweden . |
| 7612476 | 7/1978 | Sweden . |

*Primary Examiner*—Aaron J. Lewis
*Attorney, Agent, or Firm*—Pollock, Vande Sande & Priddy

[57] ABSTRACT

Breathing equipment for use under water, or in a non-respiratory atmosphere, and including a breathing mask (1), a mouth-piece or the like, and a respiratory circuit (2) with a volumetrically variable gas accumulator (7). In addition, there is included a metering bottle (26) connected to the respiratory circuit via a valve device (12), which alternatingly connects the bottle to a source (9) of fresh respiratory gas for filling the bottle and to the circuit for emptying the bottle. The valve device (12) is adapted to regulate filling and emptying the bottle (26) in response to the respiratory cycle, such that fresh respiratory gas is supplied to the circuit (2) during each such cycle. The device (12) is suitably implemented so that the amount filling the metering bottle (26) is adjusted in response to respiratory volume.

11 Claims, 2 Drawing Sheets

BREATHING APPARATUS

FIELD OF THE INVENTION

The present invention relates to breathing apparatus for use under water, or in a non-respiratory atmosphere, and includes a breathing mask, a mouth-piece or the like, a respiratory circuit with a volumetrically variable gas accumulator connected to the mask or to the mouth-piece, and a metering bottle connected to the circuit via a valve device, which alternatingly connects the metering bottle to a source of fresh respiratory gas for filling the bottle and to the circuit for emptying the bottle.

BACKGROUND OF THE INVENTION

Equipment of the kind mentioned is described, inter alia, in the Swedish patents 7502855-5 and 7612476-7. In the known apparatus breathing takes place in a closed respiratory circuit until the user has ventilated a given volume. During the period of time when this is taking place the metering bottle is filled from a source of respiratory gas. When the volume ventilated has reached its given quantity, the respiratory gas stored in the bottle is supplied to the respiratory circuit. The excess volume thus occurring in the circuit is then vented to the surroundings. A new breathing period is then started simultaneously as the bottle is filled once again with respiratory gas.

A disadvantage with the known equipment is that the replacement of used respiratory gas by fresh gas takes place at given intervals, resulting in that comparatively large gas volumes must be replaced at each occasion. This means that the oxygen content in the respiratory circuit will vary heavily, and substantially according to a function giving a saw-tooth-like graph. The oxygen content decreases substantially linearly from one filling time to the next, when it increases suddenly as the new gas is supplied. This large variation in respiratory gas quality can become a problem, particularly in the execution of energy-demanding work close to the surface.

Another disadvantage is that the comparatively large gas volumes that must be replaced very quickly at each occasion result in high flow velocities with acompanying heavy sound generation. This is a problem, inter alia, in such as mine clearing.

In addition, the simultaneous supply of a large quantity of fresh gas can cause the risk of a comparatively large portion of it being discharged directly together with the used respiratory gas.

SUMMARY OF THE INVENTION

The main object of the present invention is to provide a breathing apparatus of the kind mentioned above where, inter alia, the problems associated with large variations in oxygen content and replacing comparatively large gas quantities on each occasion have been eliminated. By reducing the gas quantities the gas flow rate may be reduced for reducing sound generation.

This object is achieved in accordance with the present invention by a breathing apparatus according to the above, in which metering of a given quantity of fresh gas occurs at every breath and suitably in proportion to the volume inhaled.

Particularly characteristic for a breathing apparatus of the kind stated in the first paragraph is that in accordance with the invention the valve device is disposed for regulating filling and emptying of the metering bottle in response to the respiratory cycle, such that fresh respiratory gas is supplied to the respiratory circuit during each cycle.

With such an apparatus is achieved that oxygen content variations in the respiratory circuit will be very small and that only a small amount of fresh respiratory gas needs to be supplied during each respiratory cycle. This results in that sound generation due to high flow rates can be eliminated or greatly reduced, and the gas vented at each occation kept very small.

It is preferred that the valve device is disposed for adjusting the degree of filling the metering bottle in response to the volume inhaled. The volume of fresh gas supplied in relation to each respiratory volume will thus be substantially constant.

Other characteristics of the invention will be apparent from the accompanying claims.

BRIEF DESCRIPTION OF THE DRAWINGS

The invention will now be described in more detail, and with reference to an embodiment shown as an example on the appended drawings.

DETAILED DESCRIPTION OF THE INVENTION

Figure 1:
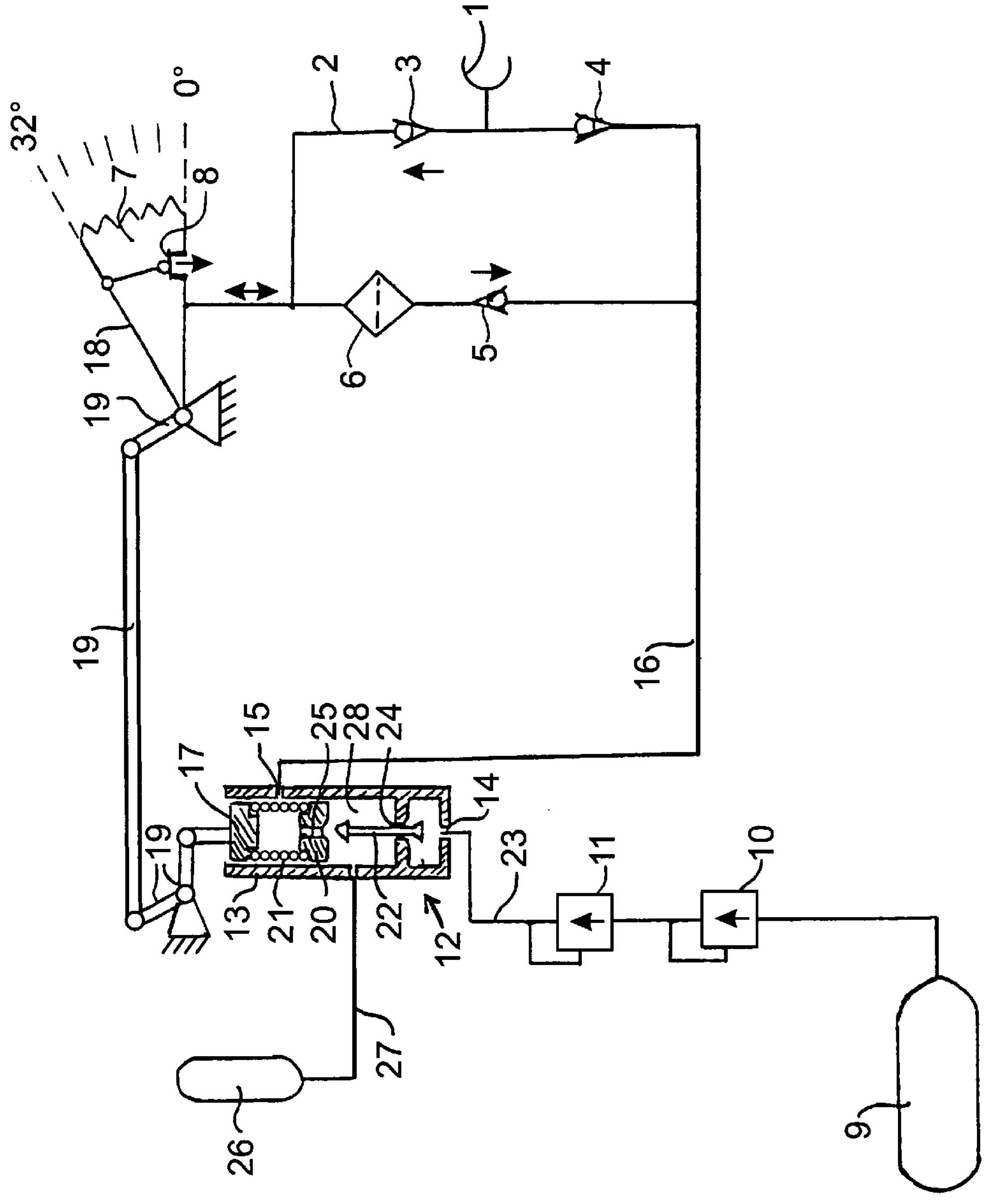
FIG. 1 schematically illustrates a breathing apparatus in accordance with the invention with a new type of valve device.

In FIG. 1, a breathing mask is denoted by the numeral 1 and is connected to a respiratory circuit 2, which also includes three non-return or check valves 3, 4, 5 and an absorber 6 having the capacity of absorbing carbon dioxide. Due to these valves, respiratory gas can only flow in the direction of the arrows in the Figures. A volumetrically variable means in the form of a bellows 7 is also connected to the circuit 2. In the illustrated example, the moveable wall 18 of the bellows can move between 0 and 32 degrees.

A fresh respiratory gas container is denoted by the numeral 9 and usually contains a mixture of oxygen and nitrogen. Respiratory gas can be supplied via a first pressure regulator 10, which lowers the pressure to about 10 bar, a second regulator 11 for lowering the pressure to about 3 bar, and a valve device 12.

The illustrated valve device 12 includes a cylindrical valve housing 13 with an inlet port 14, as well as an outlet port 15 for supplying respiratory gas to the circuit 2 via a line 16, there also being a line 27 connecting a chamber 28 in the housing to a metering bottle 26.

The housing 13 accommodates a piston 17, which moves in response to the movement of the movable wall 18 of the bellows 7, this movement being translated to the piston by a linkage system 19 such that for a decrease in bellows opening angle the piston moves into the housing a corresponding amount. As will be seen in FIG. 1, below the piston 17 there is a slide 20 coacting with the piston via a spring 21, the underside of the slide defining the upper boundary of the chamber 28. Below the slide there is a valve means 22 disposed in a transverse, intermediate wall of the housing such as to be movable up and down. The upper end of the valve means 22 is formed such as to coact with a seating at the mouth of a bore 25 in the slide, while its lower end is formed for coaction with a seating on the underside of the wall such as to close a duct 24 through the wall, under the actuation of pressure from fresh respiratory gas entering the housing 13 from a line 23 via the inlet port 14. The upper side of the wall defines the lower boundary of the chamber 28.

The apparatus described above functions in a manner which will be described below.

Starting with the operational stage shown in FIG. 1, where the bellows 7 is filled with gas, it is assumed that the wearer of the mask 1 inhales. Gas is then drawn from the bellows 7, resulting in movement of its wall 18, which is translated via the linkage system 19 to the piston 17 to move the latter a corresponding distance into the housing 13. The slide 20 simultaneously moves downwards under the action of the spring 21 and into coaction with the upper end of valve means 22. The latter is illustrated in an intermediate position, for the sake of clarity. After the inhalation, the upper end of the means 22 will close off the bore 25 passing through the slide, while the lower end of the means 22 will, as shown, have left its seat, thus opening duct 24.

Fresh respiratory gas is thus enabled to flow into the housing chamber 28 via line 23 and duct 24 and from the chamber into metering bottle 26 via line 27. When the gas pressure in chamber 28 has reached a given value, it overcomes the bias of spring 21 and the pressure in line 16 acting on the upper side of the slide 20, thus causing the slide to move upwards in the Figure. The valve means 22 will move to accompany this movement, inter alia as a result of the pressure acting on the bottom surface of the means, until duct 24 is closed off. Engagement between the upper end of the valve means and the slide will subsequently cease, thus opening duct 25 through the valve slide.

The gas supplied to the metering bottle 26 will then flow, via line 27, bore 25 and line 16 to the respiratory circuit 2, and together with the bearer's exhalation it will once again fill the bellows 7 maximally, as well as causing the valve 8 to open and exhaust as much used respiratory gas as the quantity of fresh gas let in.

At the next inhalation this fresh gas will be inhaled in the first place, and thus practically no fresh gas will be wasted.

This described cycle will be repeated for every new respiration. Since the piston 17 is urged different distances into the housing 13, in response to the relevant inhalation volume, the bias of spring 21, that must be overcome with the aid of the pressure in chamber 28 in order to move the slide 20 and open communication between bottle 26 and respiratory circuit 2, will increase in proportion to the respective distance. This signifies that the magnitude of the pressure built up in the metering bottle 26, and thereby the amount of gas stored in it, increases with increasing respiration volume. There is thus achieved an automatic adjustment of the amount of fresh respiratory gas supplied in relation to the respiration volume. The result of this is, inter alia, that the oxygen content in the respiratory circuit may be kept substantially constant independently of the respiration volume.

Figure 2:
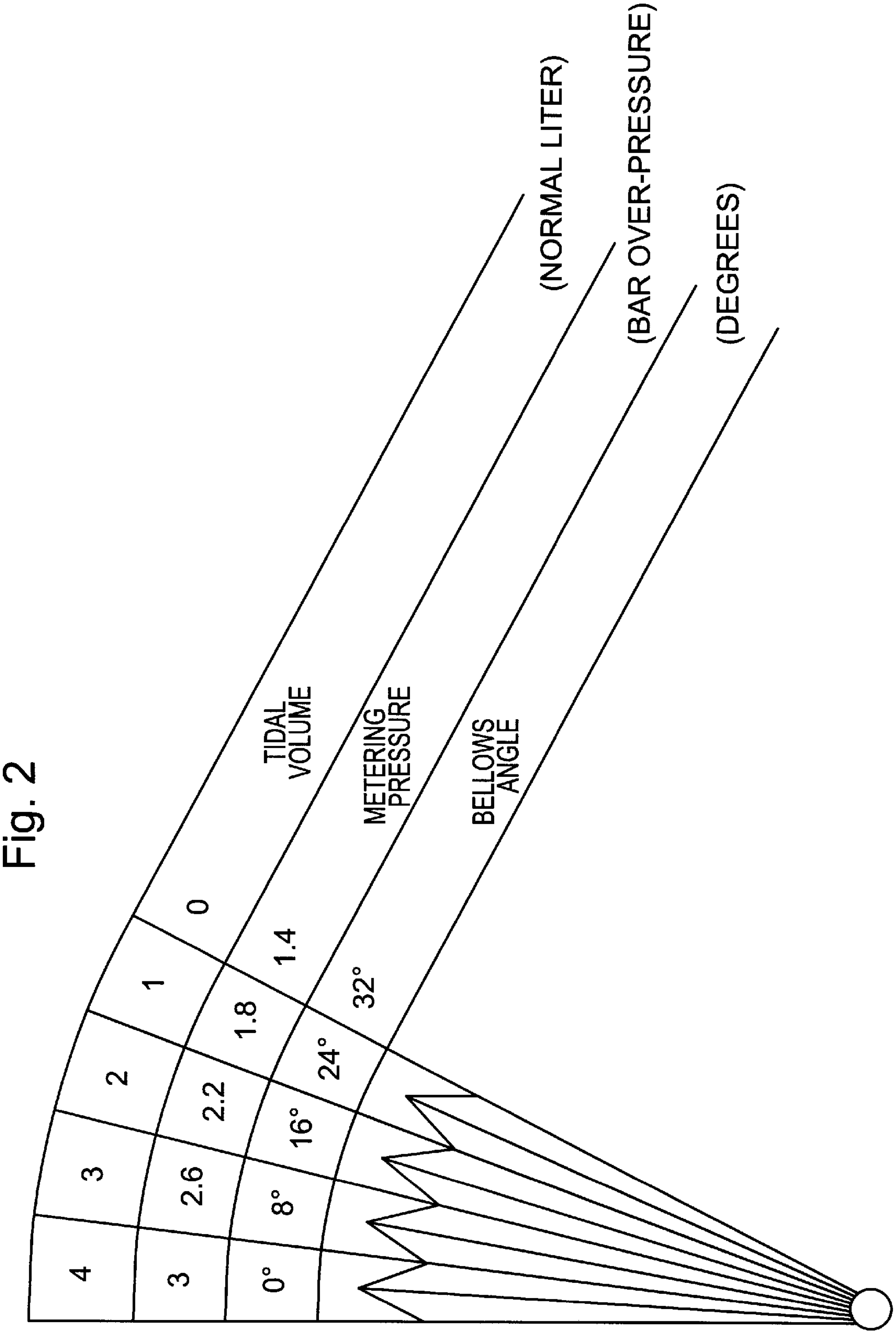
FIG. 2 is a diagram illustrating the relationships between magnitudes.

The relationship between respiration volume, i.e. so-called "tidal volume" and the pressure in metering bottle 26, is illustrated in FIG. 2. Here, the bellows angle corresponding to the respective tidal volume has also been shown. It will be seen from the Figure that a tidal volume of 2 liters will reduce the bellows angle from 32 to 16 degrees, and result in an increase in pressure in the metering bottle from an over-pressure of 1.4 to 2.2 bar. The illustrated apparatus is intended for a maximum tidal volume of 4 liters, as a respiration of 4 liters will completely empty the bellows, i.e. the angle will be zero degrees. The spring will then be compressed to such an extent that the metering bottle 26 must be filled to an over-pressure of 3 bar before the pressure is sufficient to overcome the spring bias and move the valve slide 20, so that the bore 25 to the respiratory circuit opens.

There is thus achieved in the utilization of the apparatus described that a given amount of fresh respiratory gas, determined by the respiratory volume, is supplied to the respiratory circuit during each respiratory cycle. The volume of this amount will be comparatively small, and consequently previous problems relating, inter alia, to sound generation will be reduced.

The invention has been described above in connection with a preferred embodiment. However, this may be varied in several respects within the scope of the claims. Accordingly, the bellows 7 may, for example, be replaced by another variable volume device such as a respiration bag, or the like. The volume decrease in it may be transmitted to a piston 17 or the like in some way other than with the illustrated linkage system. The valve device 12 may also be varied with respect to different details while maintaining the function described above.

In addition, the function of the described apparatus may be reversed, i.e. the metering bottle is filled during exhalation and emptied during inhalation. In this case, the linkage system 19 may be disposed, for example, so that the valve slide 20 moves in opposite directions for in- and exhalation compared with what has been described above. This results in that metering will be somewhat dependent on depth when the apparatus is used under water.

What is claimed is:

1. Breathing apparatus for use under water, or in a non-respiratory atmosphere, comprising a breathing mask or a mouth-piece a respiratory circuit with a volumetrically variable gas accumulator connected to the mask or the mouth-piece, and a metering bottle connected to the circuit via a valve device, which alternatingly connects the bottle to a source of fresh respiratory gas for filling the bottle and to the circuit for emptying the bottle, wherein the valve device is adapted to fill and empty the metering bottle during each respiratory cycle of a user and to adjust an amount of fresh respiratory gas supplied to the metering bottle in response to a respiratory volume of inhalation or exhalation of the preceding respiratory cycle, such that fresh respiratory gas is supplied to the respiratory circuit during each such cycle.

2. Apparatus as claimed in claim 1, wherein the valve device includes a pressure-controlled slide adapted to open communication between the metering bottle and the respiratory circuit at a pressure in the bottle determined by the respiratory volume.

3. Apparatus as claimed in claim 2, wherein the valve slide is disposed for opening said communication by being displaced by the pressure in the metering bottle working against a biasing force, said biasing force varying proportionally to the respiratory volume.

4. Apparatus as claimed in claim 3, wherein said biasing force is provided by a spring; and wherein the position of the spring, and thereby the spring bias that must be overcome by the pressure in the metering bottle varies in response to movement of a part of the volumetrically variable gas accumulator said part movement being determined by the respiratory volume.

5. Apparatus as claimed in claim 1, wherein the metering bottle may be put into communication with said source of respiratory gas via a duct, which may be closed by a portion of a valve means.

6. Apparatus as claimed in claim 5, wherein the valve means is disposed for lifting from a valve seating such as to open said duct consequent on movement of said valve slide, this valve slide movement being cause by the respiratory volume.

7. Apparatus as claimed in claim 6, wherein the valve means is adapted, on actuation by said valve slide, to close off a bore through said slide and thus close communication between the metering bottle and the respiratory circuit.

8. Breathing apparatus for use under water, or in a non-respiratory atmosphere, comprising a breathing mask or a mouth-piece, a respiratory circuit with a volumetrically variable gas accumulator connected to the mask or the mouth-piece, and a metering bottle connected to the circuit via a valve device, which alternatingly connects the bottle to a source of fresh respiratory gas for filling the bottle and to the circuit for emptying the bottle, wherein the valve device is adapted for regulating filling and emptying of the metering bottle in response to the respiratory cycle, such that fresh respiratory gas is supplied to the respiratory circuit during each such cycle; wherein the valve device includes a pressure-controlled slide adapted to open communication between the metering bottle and the respiratory circuit at a pressure in the bottle determined by a respiratory volume; and wherein the valve slide is disposed for opening said communication by being displaced by the pressure in the metering bottle working against a biasing force, said biasing force varying proportionally to the respiratory volume.

9. Apparatus as claimed in claim 8, wherein said biasing force is provided by a spring; and wherein the position of the spring, and thereby the spring bias that must be overcome by the pressure in the metering bottle, varies in response to the movement of a part of the volumetrically variable gas accumulator, said part movement being determined by an inhalation or exhalation.

10. Breathing apparatus for use under water, or in a non-respiratory atmosphere, comprising a breathing mask or a mouth-piece, a respiratory circuit with a volumetrically variable gas accumulator connected to the mask or the mouth-piece, and a metering bottle connected to the circuit via a valve device, which alternatingly connects the bottle to a source of fresh respiratory gas for filling the bottle and to the circuit for emptying the bottle, wherein the valve device is adapted for regulating filling and emptying of the metering bottle in response to the respiratory cycle, such that fresh respiratory gas is supplied to the respiratory circuit during each such cycle; wherein the bottle may be put into communication with said source of respiratory gas via a duct, which may be closed by a portion of a valve means; and wherein the valve means is disposed for lifting from a valve seating such as to open said duct consequent on movement of a valve slide, this valve slide movement being caused by an inhalation or exhalation.

11. Apparatus as claimed in claim 10, wherein the valve means is adapted, on actuation by said valve slide, to close off a bore through said slide and thus close communication between the metering bottle and the respiratory circuit.

* * * * *